United States Patent
Tu

[19]

[11] Patent Number: 5,968,005
[45] Date of Patent: Oct. 19, 1999

[54] DEVICES AND MEANS FOR TREATING CANKER SORES

[76] Inventor: Hosheng Tu, 2151 Palermo, Tustin, Calif. 92782

[21] Appl. No.: 09/004,110

[22] Filed: Jan. 7, 1998

[51] Int. Cl.⁶ ........................................................ A61N 1/30
[52] U.S. Cl. ................................ 604/20; 604/22; 607/102
[58] Field of Search .................... 604/20–22; 606/41–42, 606/45–50; 607/100–102

[56] References Cited

U.S. PATENT DOCUMENTS

| | | | |
|---|---|---|---|
| 3,163,166 | 12/1964 | Brant et al. | 604/20 |
| 4,702,732 | 10/1987 | Powers et al. | 604/20 |
| 4,823,791 | 4/1989 | D'Amelio et al. | 606/50 |
| 5,160,316 | 11/1992 | Henley | 604/20 |
| 5,242,441 | 9/1993 | Avitall | 606/41 |
| 5,279,543 | 1/1994 | Glikfeld et al. | 604/20 |
| 5,456,662 | 10/1995 | Edwards et al. | 604/22 |
| 5,676,648 | 10/1997 | Henley | 604/20 |
| 5,833,647 | 11/1998 | Edwards | 604/22 |

FOREIGN PATENT DOCUMENTS

| | | |
|---|---|---|
| 3-170172 | 7/1991 | Japan . |
| 1003853 | 3/1980 | U.S.S.R. . |
| 931191 | 5/1982 | U.S.S.R. . |

OTHER PUBLICATIONS

Pires LA and Huang SKS "Comparison of radiofrequency versus direct current Catheter Ablation" pp. 123–140 in Huang SKS (ed.) Radiofrequency Catheter Ablation of Cardiac Arrhythmias Armonk NY: Futura Publishing Company Inc. 1994.

*Primary Examiner*—Corrine McDermott
*Assistant Examiner*—LoAn H. Thanh

[57] ABSTRACT

A medical device for treating canker sores, wherein a flexible RF electrode means comprising a therapeutic agent delivery means, is inserted into the mouth; the electrode means being placed against and/or surrounding the canker sore region; RF energy is applied for a predetermined time and temperature to the canker sore tissue through the electrode means to cause internal lesions; and delivering a therapeutic agent to heal the tissues thereafter for a predetermined duration.

20 Claims, 6 Drawing Sheets

FIG. 3   SECTION A-A

FIG. 4

FIG. 5   SECTION B-B

FIG. 6

DEVICES AND MEANS FOR TREATING CANKER SORES

TECHNICAL FIELD

The present invention generally relates to an improved medical devices system and a means, for medical purposes, of creating lesions and, more particularly, to such devices and methods for treating the canker sores in a patient by delivering therapeutic agents to the lesion sites with controlled duration and temperature.

BACKGROUND OF THE INVENTION

Surgical procedures are usually used for the treatment of cellular tissues requiring direct contact of the target tissue with a medical instrument. Surgical procedures often lead to substantial trauma by exposing both the target and the intervening tissues. Furthermore, precise placement of a treating probe is difficult because of the location of the target tissue in the body, or the proximity of the target tissue to easily damage critical body organs, nerves, or other components.

Destruction of cellular tissues in situ has been used in the treatment of many diseases and medical conditions alone or as an adjunct to surgical removal procedures. It is often less traumatic than surgical procedures and may be the only alternative, wherein other procedures are unsafe. Ablative treatment devices have an advantage of using a destructive energy that is rapidly dissipated and reduced to a non-destructive level by conduction and convection, to forces of circulating fluids and other natural processes.

Devices using microwave energy, radiofrequency energy, ultrasonic energy, cryogenic, laser energy, and tissue destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna through a duct to the zone of treatment and applying energy diffusively through the duct wall into the surrounding tissue in the targeted directions.

Canker sores are also known as aphthous ulcerations or recurrent aphthae, which are painful sores usually formed in the mucous membrane of the mouth. The sores first appear as small red lesions that quickly whiten and then break down to form shallow ulcers. Many people, especially small children with less immunity to ulcerations, experience the pain and discomfort of canker sores for a period from several days up to a couple of weeks. While the cause of canker sores has not been identified, several pharmaceutical approaches have been taken. However, they only coat the surface of the canker sores by a relieving agent and mask the problem for temporary relief of pain and stress.

Price, Jr. in U.S. Pat. No. 5,686,095 entitled "Method of treating canker sores" teaches a method by which a fluoroquinolone is topically applied to the ulcerous area. Similarly, Alliger in U.S. Pat. No. 5,516,799 entitled "Method of treating small mouth ulcers" teaches a method of using a simple alpha hydroxy organic acid. Marcus et al. in U.S. Pat. 5,182,104 entitled "Topical virucidal composition for treatment of mucocutaneous tissue" teaches a method of topically applying composition with a virucidal impact on mucocutaneous tissue, inactivation of herpes virus and human papilloma virus as manifested in cold sores, canker sores, warts, fever blisters lesions, and aptheous ulcerations. Leeds in U.S. Pat. No. 4,466,956 entitled "Method of therapy for oral herpes simplex" discloses serial application of povidone-iodine and then application of anti-inflammatory agent. Hodosh in U.S. Pat. No. 4,191,750 entitled "Method for treating canker sores" discloses a method of applying a nitrate of potassium, lithium, sodium, magnesium, calcium or strontium. However, all the above-mentioned topical treatments are not effective because the therapeutic agent is easily swept away in the mouth of a patient. None of above-mentioned patents discloses the method for treating canker sores by heating the therapeutic fluid and forcing the heated fluid to contact the canker sores for a prolonged period treatment.

Of particular interest to the present invention are RF therapeutic protocols which have been proven to be highly effective as used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after locating the sore sites for treatment. Radiofrequency energy, when coupled with a temperature control mechanism, can supply precise energy to the device-to-tissue contact site to obtain the desired temperature for creating a lesion. It can also be used to heat the therapeutic fluid for therapeutically treating the canker sores for the optimal effect.

Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissue point for deep lesion, it is not disclosed that the needle electrode could possibly hold the heated therapeutic fluid for prolonged contact with the target tissue.

Edwards et al. in U.S. Pat. No. 5,456,662 entitled "Method for reducing snoring by RF ablation of the uvula" teaches a medical ablation method for reducing snoring wherein a flexible RF electrode wire is inserted into the uvula and RF energy is applied to the uvula tissue to cause internal lesions. Edwards et al. does not disclose a catheter to ablate an area, having capability for simultaneously delivering radiofrequency energy and a therapeutic agent.

While a radiofrequency procedure using an existing electrode device has had promising results, the device is exposed to the target tissue without prolonged therapeutic treatment by the therapeutic agent, resulting in inefficient treatment of canker sores. Therefore, there is a need for an improved device system and methods using the controllable radiofrequency energy for generating the needed heat to treat the canker sores and also to heat the therapeutic fluid. During RF energy delivery, the therapeutic agent, such as an anti-inflammatory agent or virucidal drug, is delivered to the lesion sites. By having a device with temperature control means and substance delivery capability, the canker sores can be treated therapeutically.

SUMMARY OF THE INVENTION

In general, it is an objective of the present invention to provide a method and an improved medical device for generating and controlling heat to treat the canker sores in the mucous membrane of the mouth. It is another objective of the present invention to provide a device system so that a therapeutic agent can be supplied to the canker sore sites for prolonged contact. It is another objective of the present invention to provide a method and a device for monitoring the temperature of the device and controlling the temperature through a closed-loop temperature control mechanism and/or algorithm. The location of the temperature sensor means is preferably at the proximity of the tip of the medical device. It is still another objective of this invention to provide a method and a device for treating the canker sores in a patient by delivering a therapeutic agent to the lesion sites under positive pressure, controlled time, and suitable temperature.

Briefly, heat is generated by applying a suitable energy source to a device, which is comprised of an electrode means, in contact with the body tissue. A suitable energy source may consist of radiofrequency energy, microwave energy, ultrasonic energy, alternating current energy, or laser energy. The energy can be applied to either the canker sores through the electrode means, or to the therapeutic agent to activate its effectiveness at a higher temperature. A DIP (dispersive indifferent pad) type pad that contacts the patient is connected to the Indifferent Electrode Connector on the RF generator. When using an alternating current outlet, the generator should be grounded to avoid electrical interference. Heat is controlled by the power of the RF energy delivered and by the delivery duration. The standard RF energy generator means and its applications through the electrode means to a patient are well known for those who are skilled in the art.

In one embodiment, the device is leak-proof so that the therapeutic agent, in either fluid phase or gel phase, can be forced under a positive pressure to flow inside the lumen of the device from its proximal end to the distal end. The electrode at the distal end of the device comprises a rim electrode, whereas the distal section of the device is bell-shaped or trumpet-shaped.

The method and apparatus of the present invention have several significant advantages over other known systems or techniques to treat the canker sores. In particular, the device system comprising of the electrode means using controllable RF energy as a heat source in this invention and simultaneously delivering therapeutic agent to the lesion sites, results in a more efficient therapeutic effect, which is highly desirable in its intended application on canker sores.

BRIEF DESCRIPTION OF THE DRAWINGS

Additional objectives and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
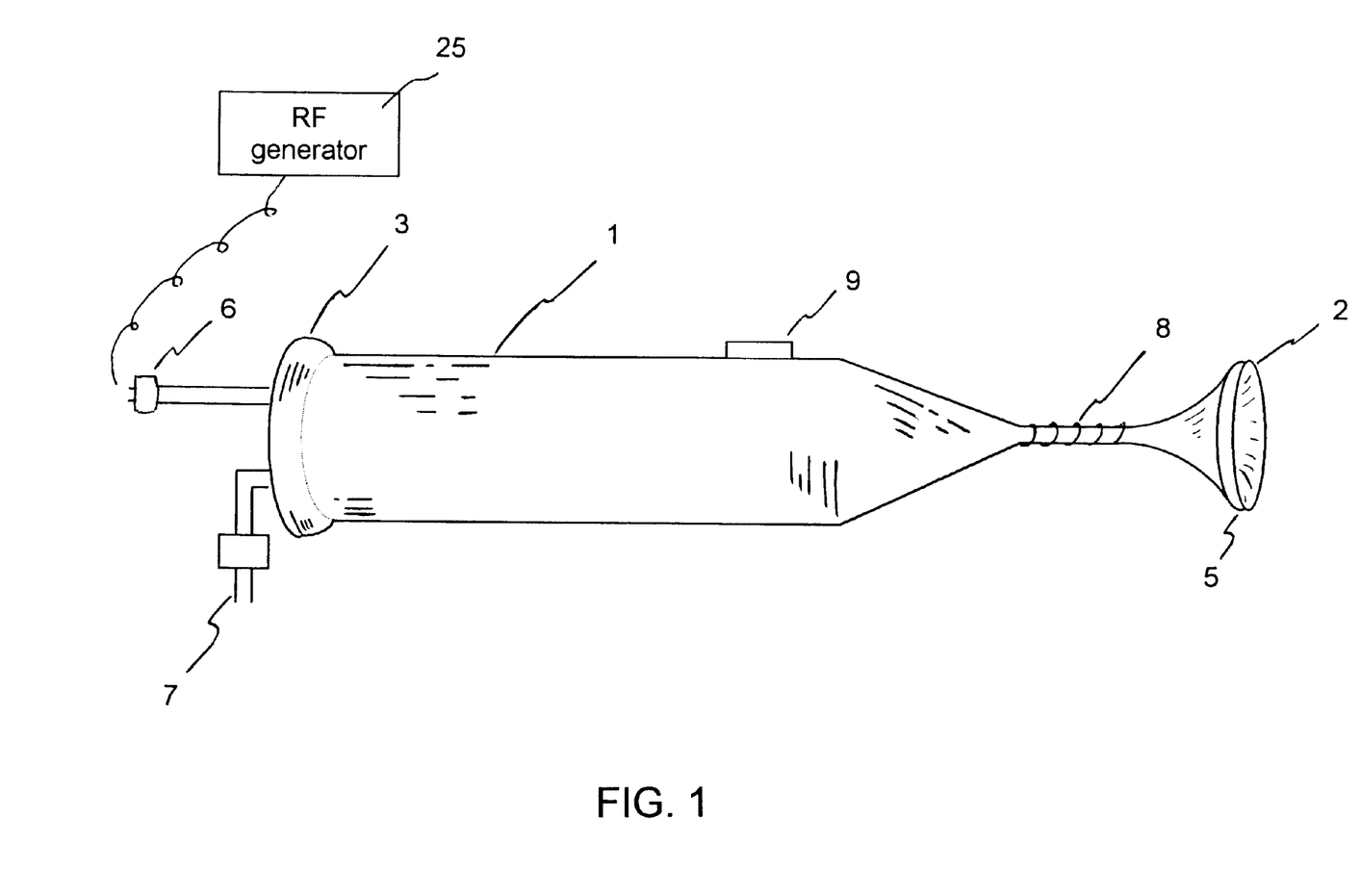
FIG. 1 is a perspective view of the device having a rim electrode means and a fluid irrigation capability, constructed in accordance with the principles of the present invention.

Referring to FIGS. 1 to 6, what is shown is an embodiment of the device system by simultaneously applying radiofrequency energy and supplying a therapeutic fluid to treat the canker sores of a patient. As shown in FIG. 1, the device system in the form of a tubular element 1 comprises a distal end 2, a proximal end 3, and at least one lumen 4 extending therebetween; wherein a rim electrode means 5 is disposed at the distal end 2, and wherein the electrode means has at least one surface zone for contacting the target tissue. The device system also comprises a connector 6 disposed at the proximal end 3 of the tubular element 1; and a means for applying radiofrequency energy from an external RF generator 25 to the electrode means 5 of the device system. In another embodiment, a fluid infusion means 7 is provided for the irrigation of a desired therapeutic agent, in either fluid phase or gel phase, to the canker sores site. The distal portion of the device comprises a coil-like element 8 so that the distal portion close to the distal end is manually bendable or steerable. A RF energy switch button 9 is located at a convenient location on the tubular element 1 for a clinician to control the "on" and "off" actions of RF energy delivery. The outer surface of said device, except the rim electrode means at its distal end, is not conductive.

Figure 2:
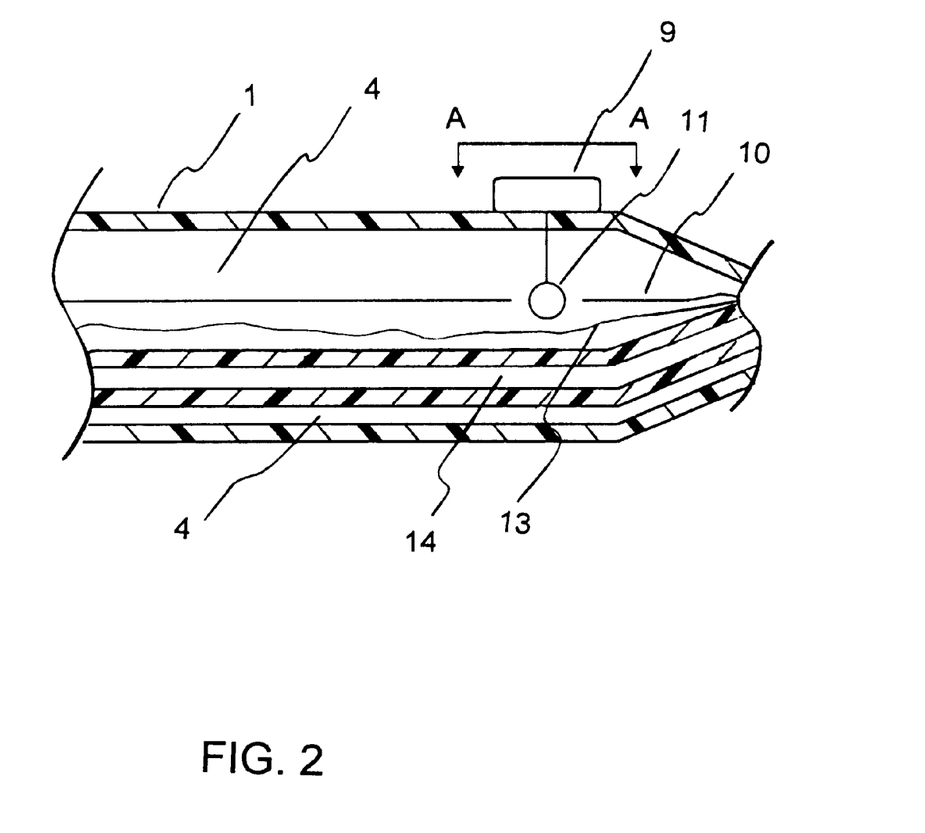
FIG. 2 is a cross-sectional view of the middle portion of the device in FIG. 1.

FIG. 2 is a cross-sectional view of the middle portion of the tubular element 1. At least one RF energy conducting wire 10 passes through the actuation mechanism 11 of the RF energy switch button 9 where the conducting wire is controlled "on" and "off" by a clinician. One end of the conducting wire 10 is secured and connected to the electrode means 5 at the distal end 2 while the other end of the conducting wire is secured to a contact pin of the connector 6, wherefrom the conducting wire is connected to an external RF generator 25 (shown in FIG. 1).

A temperature sensing means 12 is disposed close to the electrode means 5. An insulated temperature sensor wire means 13 passes from the temperature sensing means at the distal end, to an external temperature control mechanism through the outlet connector 6. The RF energy delivery is controlled by the measured temperature and by a close-loop temperature control mechanism and/or algorithm. In one embodiment, a fluid infusion means having positive pressure is provided for irrigation of the therapeutic agent. The therapeutic agent is selected from the group of heparin solution, saline solution, fluoroquinolone, lactic acid, glycolic acid, alpha hydroxy organic acids, vitamins, povidone-iodine, nitrate compounds, virucidal agents, anti-inflammatory agents, antibiotics and their mixtures. A conduit 14 is provided inside the lumen 4 for transporting the fluid or gel from the proximal end of a tubular element 1 to the distal end 2.

Figure 3:
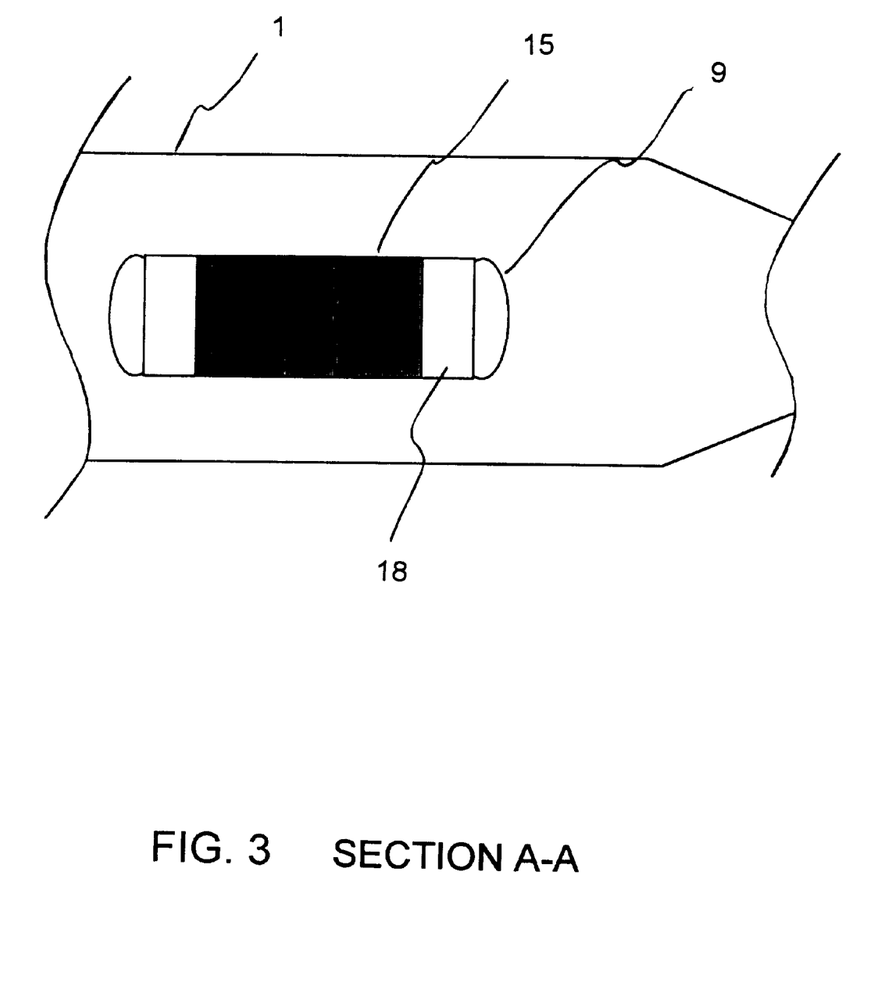
FIG. 3 is a top-view of the RF energy trigger button of FIG. 2; section A—A.

FIG. 3 is a top-view of the RF energy trigger button 9, section A—A of FIG. 2. It comprises at least one button 15, where this button controls one RF energy conducting 10. In a multiple RF delivery system, a plurality of buttons is provided for this system. Each button can individually be controlled for selected RF energy delivery to a specific electrode. In another embodiment, the rim electrode means 5 at the distal end 2 comprises a main rim electrode as the outer rim and at least one other auxiliary rim electrode inside the rim of the main rim electrode. The rim electrode means is to provide a water-tight system for the tubular element so that the therapeutic fluid can be infused and held for a prolonged duration when the rim electrode is pressed firmly against the tissue inside the mouth of a patient. The base frame 18 of the trigger button 9 is secured to the outer surface of the tubular element 1 at a convenient location for the clinician's operation.

Figure 4:
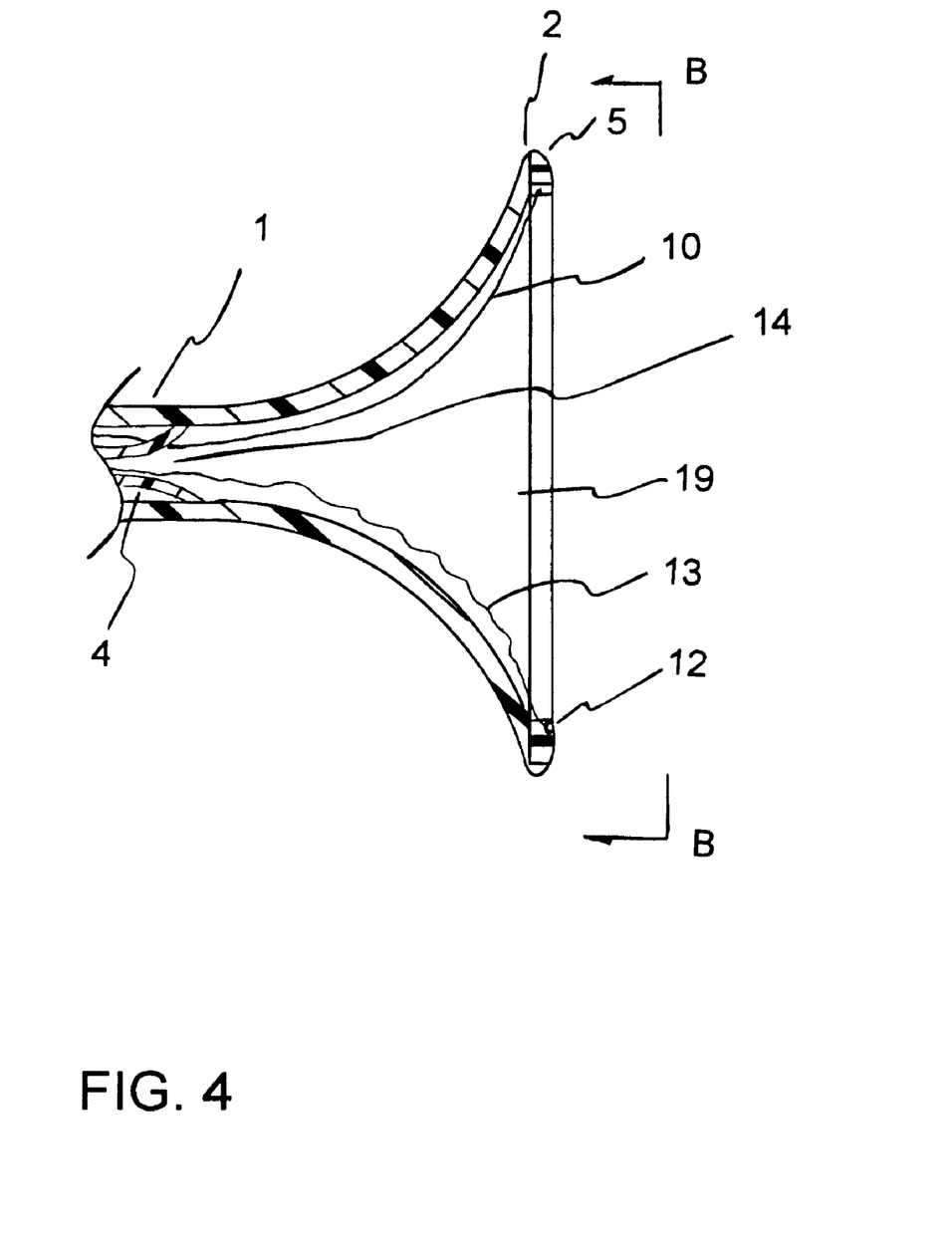
FIG. 4 is a cross-sectional view of the distal portion of the device in FIG. 1.

FIG. 4 is a cross-sectional view of the distal portion of the tubular element 1. The rim electrode means 5 is securely attached to the distal end 2 of the tubular element 1. The fluid conduit 14, located within the lumen 4 of the tubular element 1, is to provide the therapeutic fluid to the irrigation port means 19 at the distal end 2 adjacent to the electrode means 5. A temperature sensing means 12, that is disposed close to the electrode means 5, measures the temperature and transmits the temperature signal through the temperature sensor wire means 13 to an external temperature control mechanism. A conducting wire 10 is secured and connected to the electrode means 5 at the distal end 2.

Figure 5:
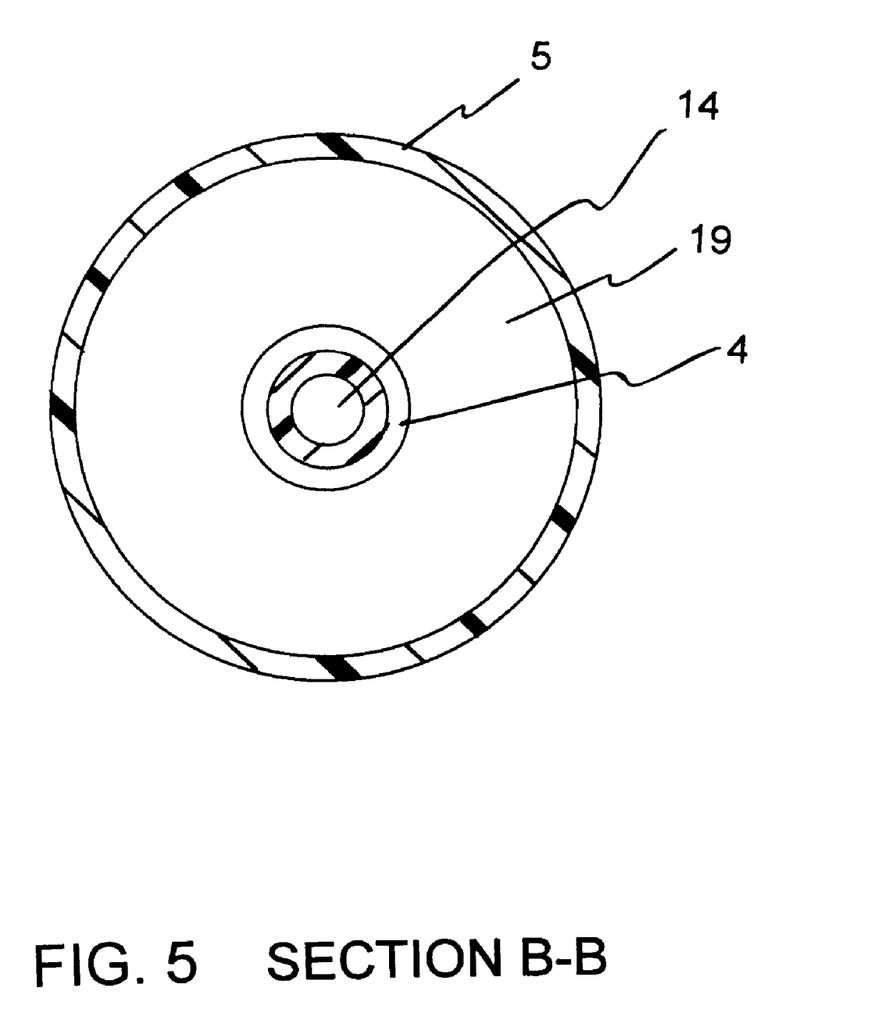
FIG. 5 is an end-view of the distal portion of the device of FIG. 4; section B—B.

FIG. 5 is an end-view of the distal portion of one type of the devices of the present invention; section B—B of FIG. 4. In this embodiment, a rim electrode constitutes the electrode means 5 of the device system. The rim electrode is connected with a conducting wire, which passes through the trigger button 9 and terminates at the connector 6 at the proximal end 3 of the tubular element. In a further embodiment, there is at least one non-conductive zone between the plurality of rim electrodes: a main outer ring electrode and other auxiliary inner rim electrodes. At least one irrigation port 19 is disposed at the distal end of the tubular element. By simultaneously applying RF energy to the rim electrode and supplying the therapeutic fluid topically, the canker sores can be treated. During the RF ablation, therapeutic fluid, in liquid or gel form, is provided through the irrigation port 19 to the canker sore region.

A method of applying a therapeutic agent to treat the canker sores of a patient comprises of inserting a device into the mouth of a patient, wherein the device has a distal section, a distal end, a proximal end, openings at both ends, and at least one lumen extending therebetween, wherein a rim electrode means is disposed at the distal end, and wherein the device is leak-proof except for the openings at the distal end and the proximal end; contacting the device against the canker sores of a patient, wherein the rim electrode means covers the target canker sore; supplying the therapeutic agent to the canker sore, wherein a positive pressure is applied to the therapeutic agent from the proximal end of the device; applying suitable energy to the rim electrode means of the device; and maintaining contact of the therapeutic agent against the canker sore for a pre-determined time duration.

Figure 6:
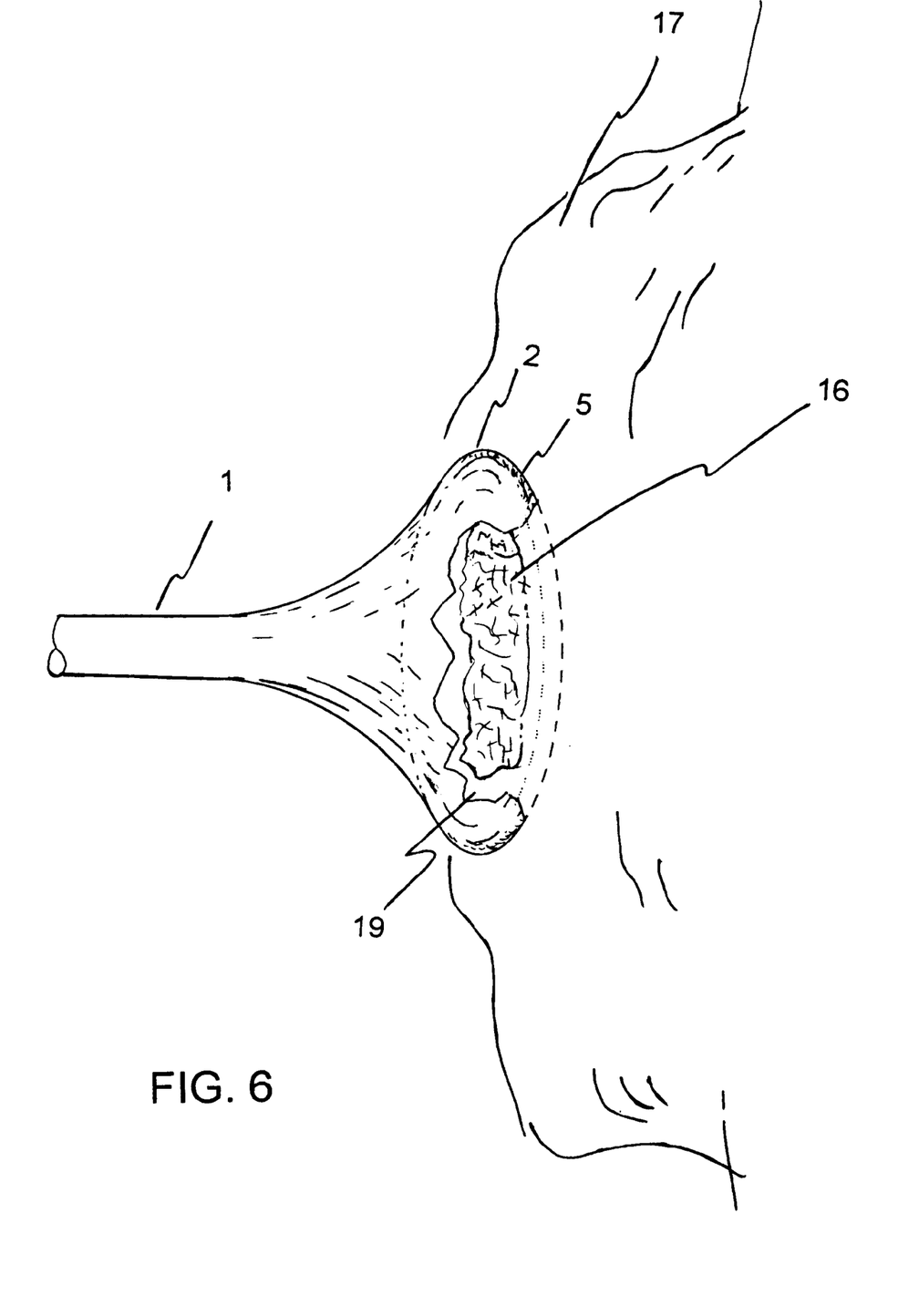
FIG. 6 shows a perspective view of a canker sore region being treated by the device and a means of the present invention.

FIG. 6 shows a perspective view of a patient's mouth, wherein a canker sore region 16 is part of the mucus membrane 17 of the mouth tissue. The tubular element 1 of the present device system comprises a distal end 2, the rim electrode means 5 and an opening 19 to cover the canker sore region 16. After firmly covering the canker sore region, the therapeutic fluid is infused and heated in-situ by the RF energy of the rim electrode 5 from an external RF generator 25. The therapeutic fluid contacts the canker sore for a prolonged duration until the symptom subsides. The RF energy generator has the capability to supply RF energy by controlling the time, power and temperature, through a separate close-loop temperature control means. The patient is connected to the RF generator through a DIP electrode to form a close-loop current system. Therefore, radiofrequency energy is applied and delivered to the target canker sore region through the electrode means of this invention. The preferred radiofrequency energy current in this invention is within the range of 50 to 2,000 kHz.

In a particular embodiment, the opening area of the distal end of the device for canker sore treatment is from 5 $mm^2$ to 100 $mm^2$ or larger. The tissue contacting electrode means comprises at least one conducting surface zone. The material for the electrode means of this invention may consist of conductive metals such as platinum, iridium, gold, silver, stainless steel, Nitinol, or an alloy of these metals.

From the foregoing description, it should now be appreciated that a medical device system for canker sores, comprising a suitable energy source and a therapeutic fluid irrigation capability has been disclosed. While the invention has been described with reference to a specific embodiment, the description is illustrative of the invention and is not to be construed as limiting the invention. Various modifications and applications may occur to those who are skilled in the art without departing from the true spirit and scope of the invention as described by the appended claims.

What is claimed is:

1. A method of applying a therapeutic agent to treat the canker sores of a patient, the method comprising:
    (a) inserting a device into the mouth of a patient, wherein the device has a distal section, a distal end, a proximal end, openings at both ends, and at least one lumen extending therebetween, wherein a rim electrode means is disposed at said distal end, and wherein said device is leak-proof except for the openings at the distal end and the proximal end;
    (b) contacting the device against the canker sores of a patient, wherein said rim electrode means covers the canker sore;
    (c) supplying a therapeutic agent to the canker sores, wherein a positive pressure is applied to said therapeutic agent from the proximal end of said device by fluid infusion means;
    (d) applying energy to the rim electrode means of the device; and
    (e) maintaining contact of the therapeutic agent against the canker sores for a pre-determined time.

2. A method of applying a therapeutic agent to treat the canker sores of a patient as in claim 1, wherein the energy is selected from the group consisting of radiofrequency energy, microwave energy, ultrasonic energy, alternating current energy, and laser energy.

3. A method of applying a therapeutic agent to treat the canker sores of a patient as in claim 2, further comprising a temperature sensor, wherein said temperature sensor is disposed at the distal end of the device.

4. A method of applying a therapeutic agent to treat the canker sores of a patient as in claim 3, further comprising a temperature controlling means, wherein a measured temperature of the temperature sensor is used as an input for the temperature controlling means to control the temperature.

5. A method of applying a therapeutic agent to treat the canker sores of a patient as in claim 2, further comprising the distal section with an outer surface, wherein the outer surface of said distal section is non-conductive.

6. A method of applying a therapeutic agent to treat the canker sores of a patient as in claim 2, further comprising the rim electrode with a cross-section, wherein the cross-sectional shape of said rim electrode means is selected from the group consisting of round shape, oval shape, x-shape, irregular shape, and wheel-tooth shape.

7. A method of applying a therapeutic agent to treat the canker sores of a patient as in claim 2, wherein said therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

8. A medical device for applying a therapeutic agent to treat the canker sores of a patient, comprising:
  (a) an elongated tubular element having a distal section, a distal end, a proximal end, openings at both ends, and at least one lumen extending therebetween, wherein rim electrode means is disposed at said distal end, and wherein said device is leak-proof except for the openings at the distal end and the proximal end;
  (b) a handle secured at said proximal end of the tubular element;
  (c) means for supplying the therapeutic agent to the distal end of said device, wherein a positive pressure is applied to said therapeutic agent from the proximal end of said device by fluid infusion means;
  (d) means for heating the therapeutic agent in situ by the energy of the rim electrode; and
  (e) means for applying energy to the rim electrode means of said device.

9. A medical device as in claim 8, wherein the energy is selected from the group consisting of radiofrequency energy, microwave energy, ultrasonic energy, alternating current energy, and laser energy.

10. A medical device as in claim 9, further comprising a temperature sensor, wherein said temperature sensor is disposed at the distal end of said device.

11. A medical device as in claim 10, further comprising temperature controlling means, wherein a measured temperature of said temperature sensor is used as an input for the temperature controlling means to control the temperature.

12. A medical device as in claim 8, wherein said distal section of the device comprises a bendable section.

13. A medical device as in claim 8, further comprising the rim electrode means, said rim electrode means is constructed of a material selected from the group consisting of platinum, iridium, gold, silver, stainless steel, Nitinol, and an alloy of their mixture.

14. A medical device as in claim 8, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

15. A medical device as in claim 9, further comprising the radiofrequency energy current being within the range of 50 to 2,000 kHz.

16. A medical device as in claim 9, further comprising the distal section with an outer surface, wherein the outer surface of said distal section is non-conductive.

17. A medical device as in claim 8, further comprising the distal section being trumpet-shaped.

18. A device system for applying a radiofrequency energy to create a lesion, comprising:
  (a) an elongated tubular element having a distal section, a distal end, a proximal end, openings at both ends, and at least one lumen extending therebetween, the electrode means disposed at said distal end, wherein said electrode means has at least one surface zone for contacting the tissue;
  (b) a handle secured at said proximal end of the tubular element;
  (c) means for supplying a therapeutic agent to the distal end of said device, wherein a positive pressure is applied to said therapeutic agent from the proximal end of said device by fluid infusion means; and
  (d) means for applying radiofrequency energy to the electrode means of said device for heating the therapeutic agent in situ, wherein radiofrequency energy is provided by a RF generator.

19. A device system as in claim 18, further comprising a temperature sensor, wherein said temperature sensor is disposed at the distal end of said device.

20. A device system as in claim 18, wherein the therapeutic agent is selected from the group consisting of heparin solution, saline solution, fluoroquinolone, lactic acid, glycolic acid, alpha hydroxy organic acids, vitamins, povidone-iodine, nitrate compounds, virucidal agents, anti-ulcer agents, anti-inflammatory agents, antibiotics, and their mixtures.

* * * * *